(12) United States Patent
Mao et al.

(10) Patent No.: US 6,811,987 B1
(45) Date of Patent: Nov. 2, 2004

(54) HUMAN CALCIUM BINDING PROTEIN AND A POLYNUCLEOTIDE ENCODING THE SAME

(75) Inventors: Yumin Mao, Shanghai (CN); Yi Xie, Shanghai (CN)

(73) Assignee: Shanghai Bio Road Gene Development, Ltd., Shanghai (CN)

( * ) Notice: Subject to any disclaimer, the term of this patent is extended or adjusted under 35 U.S.C. 154(b) by 345 days.

(21) Appl. No.: 10/130,792

(22) PCT Filed: Nov. 20, 2000

(86) PCT No.: PCT/CN00/00439

§ 371 (c)(1),
(2), (4) Date: May 23, 2002

(87) PCT Pub. No.: WO01/38521

PCT Pub. Date: May 31, 2001

(30) Foreign Application Priority Data

Nov. 23, 1999 (CN) .......................................... 99124082 A

(51) Int. Cl.⁷ ........................ G01N 33/58; A61K 38/17; C07K 14/47
(52) U.S. Cl. ........................... 435/7.1; 514/12; 530/350
(58) Field of Search ............................. 435/7.1; 514/12; 530/350

(56) References Cited

U.S. PATENT DOCUMENTS 5,871,970 A    2/1999   Hillman et al.

FOREIGN PATENT DOCUMENTS

| JP | 7-123985  | 5/1995 |
| WO | 98/26068  | 6/1998 |

OTHER PUBLICATIONS

International Search Report.

*Primary Examiner*—Robert A. Wax
(74) *Attorney, Agent, or Firm*—Crowell & Moring LLP

(57) ABSTRACT

The present invention discloses a novel polypeptide, a human binding protein 42, the polynucleotide encoding the polypeptide and the method for producing the polypeptide by DNA recombinant technology. The invention also discloses the uses of the polypeptide in methods for treating various diseases, such as malignant tumour, hemopathy. HIV infection, immunological disease, and various inflammation, etc. The invention also discloses the agonists against the polypeptide and the therapeutic action thereof. The invention also discloses the uses of the polynucleotide encoding the novel human calcium binding protein 42.

6 Claims, 1 Drawing Sheet

Identity = 59/183 (32%), Similarity = 102/183 (55%)

```
human calcium           198 AIQDVLKEKLHKRGVRILTGLGKYFQQLDKEGNGLLDKADFKQALKVFHLEVSEKDFESA  257
binding protein 42:     257 A   + L+ +     RG     + GL ++F+QLD++G+   LD   +F+Q L     L + + + E
hare R2D2 antigen:        6 ATMEKLRAQCLSRGASGIQGLARFFRQLDRDGSRSLDADEFRQGLAKLGLVLDQAEAEGV   65 human calcium           258 WLILNDNGNGKVDYGEFKRGIIGEMNEYRKSYVRKAFMKLDFNKSGSVPIINIRKCYCAK  317
binding protein 42:           + NG+G +D  EF R +    M++ R++ +   AF KLD +   G V + ++R  Y  +
hare R2D2 antigen:       66 CRKWDRNGSGTLDLEEFLRALRPPMSQAREAVIAAAFAKLDRSGDGVVTVDDLRGVYSGR  125 human calcium           318 KHSQVISGHSTEEEIKSSFLETLKVACSKSDEVSYGEFEDYYEGLSIGIVDDEDFVNILR  377
binding protein 42:          H +V SG   TE+E+    FL+       +  K   +V+   EF+DYY G+S    +   DE+FV ++
hare R2D2 antigen:      126 AHPKVRSGEWTEDEVLRRFLDNFD-SSEKDGQVTLAEFQDYYSGVSASMNTDEEFVAMMT  184 human calcium           378 TPW 380
binding protein 42:          + W
hare R2D2 antigen:      185 SAW 187
```

HUMAN CALCIUM BINDING PROTEIN AND A POLYNUCLEOTIDE ENCODING THE SAME

FIELD OF INVENTION

The invention relates to the field of biotechnology. In particular, the invention relates to a novel polypeptide, human calcium binding protein 42, and a polynucleotide sequence encoding said polypeptide. The invention also relates to the method for the preparation and use of said polynucleotide and polypeptide.

TECHNICAL BACKGROUND

Calcium functions as a medium in many biological activities in cell. These biological activities include gene regulation, cell cycle regulation, signal transduction, release of brain neurotransmitter and decomposition of glycogen involved in muscle contraction and so on. These functions are activated by calcium that are released by stimulation of extracellular signals. Calcium binds with various calcium binding protein to mediate further signals which activate other molecules and effect some specific physiological functions.

Calcium binding protein family is a very large protein super family with a calcium binding motif named "EF-hand," which is the binding site of the protein and calcium. Many calcium binding proteins have several EF-hand motifs. Approximately 250 calcium binding proteins of this type have been identified.

Calmodulin (CaM) is the most widely distributed calcium regulatory protein. Calmodulin contains four EF-hand motifs. When they bind with calcium, corresponding conformation change will occur. The activation of calmodulin will cause it to bind with other target proteins and change their activities. The main target protein of calmodulin is calmodulin-dependent protein kinase, which is involved in the regulation of smooth muscle contraction, glycogen metabolism and neurotransmitter release, while calciuneurin, another calmodulin-binding protein, is involved in brain synaptic transmission. Calmodulin plays an important role in these physiological processes. Its abnormal expression often adversely affects these normal physiological processes and leads to corresponding diseases, such as those related to abnormal release of neurotransmitter, including nervous system development disorder, nervous system degenerative diseases, neuromuscular disorder, neurocutaneous syndrome and so on.

Calcyphosine is another calcium binding protein that is co-regulated by calcium binding and phosphorylation. The dog calcyphosine P24 is a calcium binding protein with 3 EF-hand motifs and phosphorylated by cAMP-dependent protein kinase (Lefort, A., et al. 1989, EMBO, 8: 111–116). P24 is expressed in various secretory tissues such as salivary gland, lung and brain. This shows that P24 plays an important role in ion transport. In 1993, Nemoto Y. et al cloned a similar calcium binding phosphorylating protein R2D2 that regulates the signal transduction in olfactory nerve cells from hare. R2D2 has 3 EF-hand motifs and is phophorylated by cAMP-dependent protein kinase and CaM kinase (Nemoto Y. et al., 1993, J. Cell Biol., 123: 963–76). In the same year, Yasuo Nemoto et al. cloned an R2D2 antigen protein of 189 amino acid from hare. This protein has 3 EF-hand motifs, a Ca2+/calmodulin-dependent protein kinase II phosphorylation site and a cAMP-dependent kinase phosphorylation site. It is the first calcium binding protein found in olfactory sensory neurons that regulate olfactory signal transduction (Yasuo Nemoto, Jun Ikeda et al., 1993, J. Cell Biol., 123: 963–976). It is involved in the olfactory function, and its abnormal expression will lead to diseases related to olfactory organs.

The human calcium binding protein 42 of the present invention shares 32% identity and 55% similarity with the hare R2D2 antigen. They possess similar structural characteristics, that is, both of them have calcium binding EF-hand motif, Ca2+/calmodulin-dependent protein kinaseII phosphorylation site and cAMP-dependent protein kinase phosphorylation site. So both of them are calcium binding protein.

DISCLOSURE OF INVENTION

One objective of the invention is to provide an isolated novel polypeptide, i.e., a human calcium binding protein 42, and fragments, analogues and derivatives thereof.

Another objective of the invention is to provide a polynucleotide encoding said polypeptide.

Another objective of the invention is to provide a recombinant vector containing a polynucleotide encoding a human calcium binding protein 42.

Another objective of the invention is to provide a genetically engineered host cell containing a polynucleotide encoding a human calcium binding protein 42.

Another objective of the invention is to provide a method for producing a human calcium binding protein 42.

Another objective of the invention is to provide an antibody against a human calcium binding protein 42 of the invention.

Another objective of the invention is to provide mimetics, antagonists, agonists, and inhibitors for the polypeptide of the human calcium binding protein 42.

Another objective of the invention is to provide a method for the diagnosis and treatment of the diseases associated with an abnormality of human calcium binding protein 42.

The present invention relates to an isolated polypeptide, which is originated from human, and comprises a polypeptide having the amino acid sequence of SEQ ID NO: 2, or its conservative variants, or its active fragments, or its active derivatives and its analogues. Preferably, the polypeptide has the amino acid sequence of SEQ ID NO: 2.

The present invention also relates to an isolated polynucleotide, comprising a nucleotide sequence or its variant selected from the group consisting of (a) the polynucleotide encoding a polypeptide comprising the amino acid sequence of SEQ ID NO: 2; and (b) a polynucleotide complementary to the polynucleotide (a); (c) a polynucleotide that shares at least 70% homology to the polynucleotide (a) or (b). Preferably, said nucleotide sequence is selected from the group consisting of (a) the sequence of position 1022–2170 in SEQ ID NO: 1; and (b) the sequence of position 1–3829 in SEQ ID NO: 1.

The invention also includes: a vector containing a polynucleotide of said invention, especially an expression vector; a host cell genetically engineered with the vector via transformation, transduction or transfection; a method for the production of said inventive polypeptide through the process of host cell cultivation and expression product harvest.

The invention also relates to an antibody which specifically binds to the inventive polypeptide.

The invention also relates to a method for selecting compounds which could simulate, activate, antagonize, or inhibit the activity of the inventive polypeptide and the compounds obtained by the method.

The invention also relates to a method for in vitro diagnosis method of the diseases or disease susceptibility related with the abnormal expression of the inventive polypeptide. The method involves the detection of mutation in the polypeptide or its encoding polynucleotide sequence, or the determination of its quantity and/or biological activity in biological samples.

The invention also relates to pharmaceutical compositions which comprises the inventive polypeptide, its analogues, mimetics, agonists, antagonists, inhibitors, and a pharmaceutically acceptable carrier.

The invention also relates to applications of the inventive polypeptide and/or its polynucleotide for drug development to treat cancers, developmental diseases, immune diseases, or other diseases caused by abnormal expression of the inventive polypeptide.

Other aspects of the invention are apparent to the skilled in the art in view of the disclosure set forth hereinbelow.

The terms used in this specification and claims have the following meanings, unless otherwise noted.

"Nucleotide sequence" refers to oligonucleotide, nucleotide, or polynucleotide and parts of polynucleotide. It also refers to genomic or synthetic DNA or RNA, which could be single stranded or double stranded, and could represent the sense strand or the antisense strand. Similarly, the term "amino acid sequence" refers to oligopeptide, peptide, polypeptide, or protein sequence and parts of proteins. When the "amino acid sequence" in the invention is related to the sequence of a natural protein, the amino acid sequence of said "peptide" or "protein" will not be limited to be identical to the sequence of that natural protein.

"variant" of a protein or polynucleotide refers to the amino acid sequence or nucleotide sequence, respectively with one or more amino acids or one or more nucleotides changed. Such changes include deletion, insertion, and/or substitution of amino acids in the amino acid sequence, or of nucleotides in the polynucleotide sequence. These changes could be conservative and the substituted amino acid has similar structural or chemical characteristics as the original one, such as the substitution of Ile with Leu. Changes also could be not conservative, such as the substitution of Ala with Trp.

"Deletion" refers to the deletion of one or several amino acids in the amino acid sequence, or of one or several nucleotides in the nucleotide sequence.

"Insertion" or "addition" refers to the addition of one or several amino acids in the amino acid sequence, or of one or several nucleotides in the nucleotide sequence, comparing to the natural molecule. "Substitution" refers to the change of one or several amino acids, or of one or several nucleotides, into different ones without changing number of the residues.

"Biological activity" refers to structural, regulatory or biochemical characteristics of a natural molecule. Similarly, the term "immungenecity" refers to the ability of natural, recombinant, or synthetic proteins to inducing a specific immunological reaction, or of binding specific antibody in appropriate kind of animal or cell.

"Agonist" refers to molecules which regulate, but generally enhance the activity of the inventive polypeptide by binding and changing it. Agonists include proteins, nucleotides, carbohydrates or any other molecules which could bind the inventive polypeptide.

"Antagonist" or "inhibitor" refers to molecules which inhibit or down regulate the biological activity or immunogenecity the inventive polypeptide via binding to it. Antagonists or inhibitors include proteins, nucleotides, carbohydrates or any other molecules which bind to the inventive polypeptide.

"Regulation" refers to changes in function of the inventive polypeptide, including up-regulation or down-regulation of the protein activity, changes in binding specificity, changes of any other biological characteristics, functional or immune characteristics.

"Substantially pure" refers to the condition of substantially free of other naturally related proteins, lipids, saccharides, or other substances. One of ordinary skill in the art can purify the inventive polypeptide by standard protein purification techniques. Substantially pure polypeptide of the invention produces a single main band in a denaturing polyacrylamide gel. The purity of a polypeptide may also be analyzed by amino acid sequence analysis.

"Complementary" or "complementation" refers to the binding of polynucleotides by base pairing under the condition of approximate ion conditions and temperature. For instance, the sequence "C-T-G-A" could bind its complementary sequence "G-A-C-T." The complementation between two single strand molecules could be partial or complete. Homology or sequence similarity between two single strands obviously influences the efficiency and strength of the formed hybrid.

"Homology" refers to the complementary degree, which may be partially or completely homologous. "Partial homology" refers to a sequence being partially complementary to a target nucleotide. The sequence could at least partially inhibit the hybridization between a completely complementary sequence and the target nucleotide. Inhibition of hybridization could be assayed by hybridization (Southern blot or Northern blot) under less stringent conditions. Substantially complementary sequence or hybrid probe could compete with the completely complementary sequence and inhibit its hybridization with the target sequence under less stringent conditions. This doesn't mean that nonspecific binding is allowed under a less stringent condition, because specific or selective reaction is still required.

"Sequence Identity" refers to the percentage of sequence identity or similarity when two or several amino acid or nucleotide sequences are compared. Sequence identity may be determined by computer programs such as MEGALIGN (Lasergene Software Package, DNASTAR, Inc., Madison Wis.). MEGALIGN can compare two or several sequences using different methodologies such as the Cluster method (Higgins, D. G. and P. M. Sharp (1988) Gene 73: 237–244). Cluster method examines the distance between all pairs and arrange the sequences into clusters. Then the clusters are partitioned by pair or group. The sequence identity between two amino acid sequences such as sequence A and B can be calculated by the following equation:

$$\frac{\text{Number of paired identical residues between sequences } A \text{ and } B}{\text{Residue number of sequence } A - \text{number of gap residues in sequence } A - \text{number of gap residue in sequence } B} \times 100$$

Sequence identity between nucleotide sequences can also be determined by Cluster method or other well-known methods in the art such as the Jotun Hein method (Hein J., (1990) Methods in Enzymology 183: 625–645)

"Similarity" refers to the degree of identity or conservative substitution degree of amino acid residues in corresponding sites of the amino acid sequences when compared to each other. Amino acids for conservative substitution are: negative charged amino acids including Asp and Glu; positive charged amino acids including Leu, Ile and Val; Gly and Ala; Asn and Gln; Ser and Thr; Phe and Tyr.

"Antisense" refers to the nucleotide sequences complementary to a specific DNA or RNA sequence. "Antisense strand" refers to the nucleotide strand complementary to the "sense strand."

"Derivative" refers to the inventive polypeptide or the chemically modified nucleotide encoding it. This kind of modified chemical can be derived from replacement of the hydrogen atom with Alkyl, Acyl, or Amino. The nucleotide derivative can encode peptide retaining the major biological characteristics of the natural molecule.

"Antibody" refers to the intact antibody or its fragments such as Fa, F(ab')2 and Fv, and it can specifically bind to antigenic epitopes of the inventive polypeptide.

"Humanized antibody" refers to an antibody which has its amino acid sequence in non-antigen binding region replaced to mimic human antibody and still retain the original binding activity.

The term "isolated" refers to the removal of a material out of its original environment (for instance, if it's naturally produced, original environment refers to its natural environment). For example, a naturally produced polynucleotide or a polypeptide in its original host organism means it has not been "isolated," while the separation of the polynucleotide or a polypeptide from its coexisting materials in natural system means it was "isolated." This polynucleotide may be a part of a vector, or a part of a compound. Since the vector or compound is not part of its natural environment, the polynucleotide or peptide is still "isolated."

As used herein, the term "isolated" refers to a substance which has been isolated from the original environment. For naturally occurring substance, the original environment is the natural environment. For example, the polynucleotide and polypeptide in a naturally occurring state in the viable cells are not isolated or purified. However, if the same polynucleotide and polypeptide have been isolated from other components naturally accompanying them, they are isolated or purified.

As used herein, "isolated human calcium binding protein 42," means that human calcium binding protein 42 does not essentially contain other proteins, lipids, carbohydrate or any other substances associated therewith in nature. The skilled in the art can purify human calcium binding protein 42, by standard protein purification techniques. The purified polypeptide forms a single main band on a non-reducing PAGE gel. The purity of human calcium binding protein 42 can also be analyzed by amino acid sequence analysis.

The invention provides a novel polypeptide—human calcium binding protein 42, which comprises the amino acid sequence shown in SEQ ID NO: 2. The polypeptide of the invention may be a recombinant polypeptide, natural polypeptide, or synthetic polypeptide, preferably a recombinant polypeptide. The polypeptide of the invention may be a purified natural product or a chemically synthetic product. Alternatively, it may be produced from prokaryotic or eukaryotic hosts, such as bacterial, yeast, higher plant, insect, and mammal cells, using recombinant techniques. Depending on the host used in the protocol of recombinant production, the polypeptide of the invention may be glycosylated or non-glycosylated. The polypeptide of the invention may or may not comprise the starting Met residue.

The invention further comprises fragments, derivatives and analogues of human calcium binding protein 42. As used in the invention, the terms "fragment," "derivative" and "analogue" mean the polypeptide that essentially retains the same biological functions or activity of human calcium binding protein 42 of the invention. The fragment, derivative or analogue of the polypeptide of the invention may be (i) one in which one or more of the amino acid residues are substituted with a conserved or non-conserved amino acid residue (preferably a conserved amino acid residue) and such substituted amino acid residue may or may not be one encoded by the genetic code; or (ii) one in which one or more of the amino acid residues are substituted with other residues, including a substituent group; or (iii) one in which the mature polypeptide is fused with another compound, such as a compound to increase the half-life of the polypeptide (for example, polyethylene glycol); or (iv) one in which additional amino acids are fused to the mature polypeptide, such as a leader or secretory sequence or a sequence which is employed for purification of the mature polypeptide or a proprotein sequence. Such fragments, derivatives and analogs are deemed to be within the scope of the skilled in the art from the teachings herein.

The invention provides an isolated nucleic acid or polynucleotide which comprises the polynucleotide encoding an amino acid sequence of SEQ ID NO: 2. The polynucleotide sequence of the invention includes the nucleotide sequence of SEQ ID NO: 1. The polynucleotide of the invention was identified in a human embryonic brain cDNA library. Preferably, it comprises a full-length polynucleotide sequence of 3829 bp, whose ORF (1022–2170) encodes 382 amino acids. Based on amino acid homology comparison, it is found that the encoded polypeptide is 32% homologous to hare R2D2 antigen. This novel human calcium binding protein 42 has similar structures and biological functions to those of the hare R2D2 antigen.

The polynucleotide according to the invention may be in the forms of DNA or RNA. The forms of DNA include cDNA, genomic DNA, and synthetic DNA, etc., in single stranded or double stranded form. DNA may be an encoding strand or a non-encoding strand. The coding sequence for mature polypeptide may be identical to the coding sequence shown in SEQ ID NO: 1, or is a degenerate sequence. As used herein, the term "degenerate sequence" means a sequence which encodes a protein or peptide comprising a sequence of SEQ ID NO: 2 and which has a nucleotide sequence different from the sequence of coding region in SEQ ID NO: 1.

The polynucleotide encoding the mature polypeptide of SEQ ID NO: 2 includes those encoding only the mature polypeptide, those encoding mature polypeptide plus various additional coding sequence, the coding sequence for mature polypeptide (and optional additional encoding sequence) plus the non-coding sequence.

The term "polynucleotide encoding the polypeptide" includes polynucleotides encoding said polypeptide and polynucleotides comprising additional coding and/or non-coding sequences.

The invention further relates to variants of the above polynucleotides which encode a polypeptide having the same amino acid sequence of invention, or a fragment, analogue and derivative of said polypeptide. The variant of the polynucleotide may be a naturally occurring allelic variant or a non-naturally occurring variant. Such nucleotide variants include substitution, deletion, and insertion variants. As known in the art, an allelic variant may have a substitution, deletion, and insertion of one or more nucleotides without substantially changing the functions of the encoded polypeptide.

The present invention further relates to polynucleotides, which hybridize to the hereinabove-described sequences, that is, there is at least 50% and preferably at least 70% identity between the sequences. The present invention particularly relates to polynucleotides, which hybridize to the polynucleotides of the invention under stringent conditions. As herein used, the term "stringent conditions" means the following conditions: (1) hybridization and washing under low ionic strength and high temperature, such as 0.2×SSC, 0.1% SDS, 60° C.; or (2) hybridization after adding denaturants, such as 50% (v/v) formamide, 0.1% bovine serum/0.1% Ficoll, 42° C.; or (3) hybridization only when the homology of two sequences at least 95%, preferably 97%. Further, the polynucleotides which hybridize to the hereinabove described polynucleotides encode a polypeptide which retains the same biological function and activity as the mature polypeptide of SEQ ID NO: 2.

The invention also relates to nucleic acid fragments hybridized with the hereinabove sequence. As used in the present invention, the length of the "nucleic acid fragment" is at least more than 10 bp, preferably at least 20–30 bp, more preferably at least 50–60 bp, and most preferably at least 100 bp. The nucleic acid fragment can be used in amplification techniques of nucleic acid, such as PCR, so as to determine and/or isolate the polynucleotide encoding human calcium binding protein 42.

The polypeptide and polynucleotide of the invention are preferably in the isolated form, preferably purified to be homogenous.

According to the invention, the specific nucleic acid sequence encoding human calcium binding protein 42 can be obtained in various ways. For example, the polynucleotide is isolated by hybridization techniques well-known in the art, which include, but are not limited to 1) the hybridization between a probe and genomic or cDNA library so as to select a homologous polynucleotide sequence, and 2) antibody screening of expression library so as to obtain polynucleotide fragments encoding polypeptides having common structural features.

According to the invention, DNA fragment sequences may further be obtained by the following methods: 1) isolating double-stranded DNA sequence from genomic DNA; and 2) chemical synthesis of DNA sequence so as to obtain the double-stranded DNA.

Among the above methods, the isolation of genomic DNA is least frequently used. A commonly used method is the direct chemical synthesis of DNA sequence. A more frequently used method is the isolation of cDNA sequence. Standard methods for isolating the cDNA of interest is to isolate mRNA from donor cells that highly express said gene followed by reverse transcription of mRNA to form plasmid or phage cDNA library. There are many established techniques for extracting mRNA and the kits are commercially available (e.g. Qiagene). Conventional method can be used to construct cDNA library (Sambrook, et al., Molecular Cloning, A Laboratory Manual, Cold Spring Harbor Laboratory. New York, 1989). The cDNA libraries are also commercially available. For example, Clontech Ltd. has various cDNA libraries. When PCR is further used, even an extremely small amount of expression products can be cloned.

Numerous well-known methods can be used for screening for the polynucleotide of the invention from cDNA library. These methods include, but are not limited to, (1) DNA-DNA or DNA-RNA hybridization; (2) the appearance or loss of the function of the marker-gene; (3) the determination of the level of human calcium binding protein 42 transcripts; (4) the determination of protein product of gene expression by immunology methods or the biological activity assays. The above methods can be used alone or in combination.

In method (1), the probe used in the hybridization could be homologous to any portion of polynucleotide of invention. The length of probe is typically at least 10 nucleotides, preferably at least 30 nucleotides, more preferably at least 50 nucleotides, and most preferably at least 100 nucleotides. Furthermore, the length of the probe is usually less than 2000 nucleotides, preferably less than 1000 nucleotides. The probe usually is the DNA sequence chemically synthesized on the basis of the sequence information. Of course, the gene of the invention itself or its fragment can be used as a probe. The labels for DNA probe include, e.g., radioactive isotopes, fluoresceins or enzymes such as alkaline phosphatase.

In method (4), the detection of the protein products expressed by human calcium binding protein 42 gene can be carried out by immunology methods, such as Western blotting, radioimmunoassay, and ELISA.

The method of amplification of DNA/RNA by PCR (Saiki, et al. Science 1985; 230:1350–1354) is preferably used to obtain the polynucleotide of the invention. Especially when it is difficult to obtain the full-length cDNA, the method of RACE (RACE-cDNA terminate rapid amplification) is preferably used. The primers used in PCR can be selected according to the polynucleotide sequence information of the invention disclosed herein, and can be synthesized by conventional methods. The amplified DNA/RNA fragments can be isolated and purified by conventional methods such as gel electrophoresis.

Sequencing of polynucleotide sequence of the gene of the invention or its various DNA fragments can be carried out by the conventional dideoxy sequencing method (Sanger et al. PNAS, 1977, 74: 5463–5467). Sequencing of polynucleotide sequence can also be carried out using the commercially available sequencing kits. In order to obtain the full-length cDNA sequence, it is necessary to repeat the sequencing process. Sometimes, it is needed to sequence the cDNA of several clones to obtain the full-length cDNA sequence.

The invention further relates to a vector comprising the polynucleotide of the invention, a genetically engineered host cell transformed with the vector of the invention or directly with the sequence encoding human calcium binding protein 42, and a method for producing the polypeptide of the invention by recombinant techniques.

In the present invention, the polynucleotide sequences encoding human calcium binding protein 42 may be inserted into a vector to form a recombinant vector containing the polynucleotide of the invention. The term "vector" refers to a bacterial plasmid, bacteriophage, yeast plasmid, plant virus or mammalian virus such as adenovirus, retrovirus or any other vehicle known in the art. Vectors suitable for use in the present invention include, but are not limited to the T7-based expression vector for expression in bacteria (Rosenberg, et al., Gene, 56:125, 1987), the pMSXND expression vector for expression in mammalian cells (Lee and Nathans, J Biol. Chem., 263:3521, 1988) and baculovirus-derived vectors for expression in insect cells. Any plasmid or vector can be used to construct the recombinant expression vector as long as it can replicate and is stable in the host. One important feature of an expression vector is that the expression vector typically contains an origin of replication, a promoter, a marker gene as well as translation regulatory components.

Methods known in the art can be used to construct an expression vector containing the DNA sequence of human calcium binding protein 42 and appropriate transcription/translation regulatory components. These methods include in vitro recombinant DNA technique, DNA synthesis technique, in vivo recombinant technique and so on (Sambroook, et al. Molecular Cloning, a Laboratory Manual, Cold Spring Harbor Laboratory, New York, 1989). The DNA sequence is operatively linked to a proper promoter in an expression vector to direct the synthesis of mRNA. Exemplary promoters are lac or trp promoter of *E. coli*; PL promoter of λ phage; eukaryotic promoters including CMV immediate early promoter, HSV thymidine kinase promoter, early and late SV40 promoter, LTRs of retrovirus, and other known promoters which control gene expression in the prokaryotic cells, eukaryotic cells or viruses. The expression vector may further comprise a ribosome binding site for initiating translation, transcription terminator and the like. Transcription in higher eukaryotes is increased by inserting an enhancer sequence into the vector. Enhancers are cis-acting elements of DNA, usually about from 10 to 300 bp in length that act on a promoter to increase gene transcription level. Examples include the SV40 enhancer on the late side of the replication origin 100 to 270 bp, the polyoma enhancer on the late side of the replication origin, and adenovirus enhancers.

Further, the expression vector preferably comprises one or more selective marker genes to provide a phenotype for the selection of the transformed host cells, e. g. , the dehydrofolate reductase, neomycin resistance gene and GFP (green flurencent protein) for eukaryotic cells, as well as tetracycline or ampicillin resistance gene for *E. coli*.

An ordinarily skilled in the art know clearly how to select appropriate vectors, transcriptional regulatory elements, e.g., promoters, enhancers, and selective marker genes.

According to the invention, polynucleotide encoding human calcium binding protein 42 or recombinant vector containing said polynucleotide can be transformed or transfected into host cells to construct genetically engineered host cells containing said polynucleotide or said recombinant vector. The term "host cell" means prokaryote, such as bacteria; or primary eukaryote, such as yeast; or higher eukaryotic, such as mammalian cells. Representative examples are bacterial cells, such as *E. coli*, Streptomyces, *Salmonella typhimurium*; fungal cells, such as yeast; plant cells; insect cells such as Drosophila S2 or Sf9; animal cells such as CHO, COS or Bowes melanoma.

Transformation of a host cell with the DNA sequence of invention or a recombinant vector containing said DNA sequence may be carried out by conventional techniques as are well known to those skilled in the art. When the host is prokaryotic, such as *E. coli*, competent cells, which are capable of DNA uptake, can be prepared from cells harvested after exponential growth phase and subsequently treated by the CaCl2 method using procedures well known in the art. Alternatively, MgCl2 can be used. Transformation can also be carried out by electroporation, if desired. When the host is an eukaryote, transfection methods as well as calcium phosphate precipitation may be used. Conventional mechanical procedures such as micro-injection, electroporation, or liposome-mediated transfection may also be used.

The recombinant human calcium binding protein 42 can be expressed or produced by the conventional recombinant DNA technology (Science, 1984; 224:1431), using the polynucleotide sequence of the invention. The steps generally include:

(1) transfecting or transforming the appropriate host cells with the polynucleotide (or variant) encoding human calcium binding protein 42 of the invention or the recombinant expression vector containing said polynucleotide;

(2) culturing the host cells in an appropriate medium; and (3) isolating or purifying the protein from the medium or cells.

In Step (2) above, depending on the host cells used, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In Step (3), the recombinant polypeptide may be included in the cells, or expressed on the cell membrane, or secreted out of the cell. If desired, physical, chemical and other properties can be utilized in various isolation methods to isolate and purify the recombinant protein. These methods are well-known to those skilled in the art and include, but are not limited to conventional renaturation treatment, treatment by a protein precipitant (such as salt precipitation), centrifugation, cell lysis by osmosis, sonication, supercentrifugation, molecular sieve chromatography or gel chromatography, adsorption chromatography, ion exchange chromatography, HPLC, and any other liquid chromatography, and a combination thereof.

BRIEF DESCRIPTION OF THE DRAWINGS

The following drawings are provided to illustrate the embodiment of the invention, not to limit the scope of invention defined by the claims.

FIG. 1 shows an alignment comparison of amino acid sequences of human calcium binding protein 42 of the invention and hare R2D2 antigen. The upper sequence is human calcium binding protein 42, and the lower sequence is hare R2D2 antigen. The identical and similar amino acids are indicated by a one-letter code of amino acid and "+" respectively.

FIG. 2 shows the SDS-PAGE of the isolated human calcium binding protein 42, which has a molecular weight of 42 kDa. The isolated protein band is marked with an arrow.

BEST MODE FOR CARRYING OUT THE INVENTION

The invention is further illustrated by the following examples. It is appreciated that these examples are only intended to illustrate the invention, not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLE 1

Cloning of Human Calcium Binding Protein 42 Gene

Total RNA from a human embryonic brain was extracted by the one-step method with guanidinium isocyanate/phenol/chloroform. The poly(A) mRNA was isolated from the total RNA with Quik MRNA Isolation Kit (Qiegene). CDNA was prepared by reverse transcription with 2 μg poly(A) mRNA. The cDNA fragments were inserted into the polyclonal site of pBSK(+) vector (Clontech) using Smart cDNA cloning kit (Clontech) and then transformed into DH5α to form the cDNA library. The 5'- and 3'-ends of all clones were sequenced with Dye terminate cycle reaction sequencing kit (Perkin-Elmer) and ABI 377 Automatic Sequencer (Perkin-Elmer). The sequenced cDNA were compared with the public database of DNA sequences (Genebank) and the DNA sequence of one clone 0896b12 was found to be a novel DNA sequence. The inserted cDNA sequence of clone 0896b12 was dual-directionally sequenced with a serial of synthesized primers. It was indicated that the full length cDNA contained in clone 0896b12 was 2861 bp (SEQ ID NO: 1) with a 1148 bp ORF located in positions 1022–2170 which encoded a novel protein (SEQ ID NO:2). This clone was named pBS-0896b12 and the encoded protein was named human calcium binding protein 42.

EXAMPLE 2

Homology Search of cDNA Clone

The homology research of the DNA sequence and its protein sequence of human calcium binding protein 42 of the invention were performed by Blast (Basic local Alignment search tool) (Altschul, S. F. et al. J.Mol.Biol. 1990; 215: 403–10) in databases such as Genbank, Swissport, etc. The most homologous gene to human calcium binding protein 42 of the invention is known hare R2D2 antigen. The Genbank accession number of its encoded protein is X97966. The alignment result of the protein was shown in FIG. 1. Two proteins are highly homologous with an identity of 32% and a similarity of 55%.

EXAMPLE 3

Cloning Human Calcium Binding Protein 42 Gene by RT-PCR

The template was total RNA extracted from a human embryonic brain. The reverse transcription was carried out with oligo-dT primer to produce cDNAs. After cDNA purified with Qiagen Kit, PCR was carried out with the following primers:

Primer 1: 5'-GGGGGAGAGGAGGGGAAA
GCTA-3' (SEQ ID NO: 3)

Primer 2: 5'-GTATAACAGACTATACATTTTC-3' (SEQ ID NO: 4)

Primer 1 is the forward sequence started from position 1 of 5' end of SEQ ID NO: 1.

Primer 2 is the reverse sequence of the 3' end of SEQ ID NO: 1.

The amplification condition was a 50 ul reaction system containing 50 mmol/L KCl1, 10 mmol/L Tris-Cl (pH8.5), 1.5 mmol/L MgCl$_2$, 200 umol/L dNTP, 10 pmol of each primer, 1 U Taq DNA polymerase(Clontech). The reaction was performed on a PE 9600 DNA amplifier with the following parameters: 94° C. 30 sec, 55° C. 30 sec, and 72° C. 2 min for 25 cycles. β-actin was used as a positive control, and a blank template, as a negative control in RT-PCR. The amplified products were purified with a QIAGEN kit, and linked with a pCR vector (Invitrogen) using a TA Cloning Kit. DNA sequencing results show that the DNA sequence of PCR products was identical to nucleotides 1–3829 bp of SEQ ID NO: 1.

EXAMPLE 4

Northern Blotting of Expression of Human Calcium Binding Protein 42 Gene

Total RNA was extracted by one-step method (Anal. Biochem 1987, 162, 156–159) with guanidinium isocyanate-phenol-chloroform. That is, homogenate the organize using 4M guanidinium isocyanate-25 mM sodium citrate, add 1 volume phenol and 1/5 volume chloroform-isoamyl alcohol(49:1), centrifuge after mixing. Take out the water phase, add 0.8 volume isopropyl alcohol, then centrifuge the mixture. Wash the RNA precipitation using 70% ethanol, then dry, then dissolve it in the water. 20 µg RNA was electrophoresed on the 1.2% agarose gel containing 20 mM 3-(N-morpholino) propane sulfonic acid(pH 7. 0)-5 mM sodium acetate-imM EDTA-2.2M formaldehyde. Then transfer it to a nitrocellulose filter. Prepare the $^{32}$P-labelled DNA probe with α-$^{32}$P dATP by random primer method. The used DNA probe is the coding sequence (1022 bp–2170 bp) of human calcium binding protein 42 amplified by PCR indicated in FIG. 1. The nitrocellulose filter with the transferred RNA was hybridized with the $^{32}$P-labelled DNA probe (2×10$^6$ cpm/ml) overnight in a buffer containing 50% formamide-25 mM KH$_2$PO$_4$(Ph7.4)-5×Denhardt's solution and 200 µg /ml salmine. Then wash the filter in the 1×SSC–0.1% SDS, at 55° C., for 30 min. Then analyze and quantitative determinate using Phosphor Imager.

EXAMPLE 5

In vitro Expression, Isolation and Purification of Recombinant Human Calcium Binding Protein 42

A pair of primers for specific amplification was designed based on SEQ ID NO: 1 and the encoding region in FIG. 1, the sequences are as follows:

Primer3:5'-CCCCATATGATGATAGACCACTTATCTAGG
GCTG-3' (SEQ ID NO: 5)

Primer4:5'-CCCCATATGATGATAGACCACTTATCTA
GGGCTG-3' (SEQ ID NO: 6)

These two primers contain a NdeI and BamHI cleavage site on the 5' end respectively. Within the sites are the coding sequences of the 5' and 3' end of the desired gene. NdeI and BamHI cleavage sites were corresponding to the selective cleavage sites on the expression vector pET-28b(+) (Novagen, Cat. No. 69865.3). PCR amplification was performed with the plasmid pBS-0896b12 containing the full-length target gene as a template. The PCR reaction was subject to a 50 µl system containing 10 pg pBS-0896b12 plasmid, 10 pmol of Primer-3 and 10 pmol of Primer-4, 1 µl of Advantage polymerase Mix (Clontech). The parameters of PCR were 94° C. 20 sec, 60° C. 30 sec, and 68° C. 2 min for 25 cycles. After digesting the amplification products and the plasmid pET-28(+) by NcoI and BamHI, the large fragments were recovered and ligated with T4 ligase. The ligated product was transformed into E. coli DH5α with the calcium chloride method. After cultured overnight on a LB plate containing a final concentration of 30 µg/ml kanamycin, positive clones were selected out using colony PCR and then sequenced. The positive clone (pET-0896b12) with the correct sequence was selected out and the recombinant plasmid thereof was transformed into BL21(DE3) plySs (Novagen) using the calcium chloride method. In a LB liquid medium containing a final concentration of 30 µg/ml of kanamycin, the host bacteria BL21(pET-0896b12) were cultured at 37° C. to the exponential growth phase, then IPTG were added with the final concentration of 1 mmol/L, the cells were cultured for another 5 hours, and then centrifuged to harvest the bacteria. After the bacteria were sonicated, the supernatant was collected by centrifugation. Then the purified desired protein-human calcium binding protein 42 was obtained by a His.Bind Quick Cartridge (Novagen) affinity column with binding 6His-Tag. SDS-PAGE showed a single band at 42 kDa (FIG. 2). The band was transferred onto the PVDF membrane and the N terminal amino acid was sequenced by Edams Hydrolysis, which shows that the first 15 amino acids on N-terminus were identical to those in SEQ ID NO: 2.

EXAMPLE 6

Preparation of Antibody Against Human Calcium Binding Protein 42

The following specific human calcium binding protein 42 polypeptide was synthesized by a polypeptide synthesizer (PE-ABI): NH2-Met-Ile-Asp-His-Leu-Ser-Arg-Ala-Val-Ile-Ser-Asp-Pro-Glu-Gln-COOH (SEQ ID NO: 7). The polypeptide was conjugated with hemocyanin and bovine serum albumin (BSA) respectively to form two composites (See Avrameas et al., Immunochemistry, 1969, 6:43). 4 mg of hemocyanin-polypeptide composite was used to immunize rabbit together with Freund's complete adjuvant. The rabbit was re-immunized with the hemocyanin-polypeptide composite and Freund's incomplete adjuvent 15 days later. The titer of antibody in the rabbit sera was determined with a titration plate coated with 15 µg/ml BSA-polypeptide composite by ELISA. The total IgG was isolated from the sera of an antibody positive rabbit with Protein A-Sepharose. The polypeptide was bound to Sepharose 4B column activated by cyanogen bromide. The antibodies against the polypeptide were isolated from the total IgG by affinity chromatography. The immunoprecipitation approved that the purified antibodies could specifically bind to human calcium binding protein 42.

EXAMPLE 7

Application of the Polynucleotide Fragments of the Invention As Hybridization Probes Oligonucleotides probes selected from the polynucleotide of the invention have many applications. The probe could be used to determine the existence of polynucleotide of the invention or its homologous polynucleotide sequences by hybridization with genomic, or cDNA library of normal or clinical tissues from varied sources. The probes could be further used to determine whether polynucleotide of the invention or its homologous polynucleotide sequences are abnormally expressed in cells from normal or clinical tissues.

The purpose of the following example is to select suitable oligonucletide fragments from SEQ ID NO:1 as hybrid probes to apply in membrane hybridization to determine whether there is polynucleotide of the invention or its homologous polynucleotide sequences in sample tissues. Membrane hybridization methods include dot blot, Southern blot, Northern blot, and replica hybridization. All methods follow nearly the same steps after the polynucleotide samples are immobilized on membranes. These steps are: membranes with immobilized samples are prehybridized in hybridization buffer not containing probes to block nonspecific binding sites of the membranes. Then the prehybridization buffer is replaced by hybridization buffer containing labeled probes and incubation is carried out at the appropriate temperature so probes hybridize with the target nucleotides. Free probes are washed off by a series of washing steps after the hybridization step. A high-stringency washing condition (relatively low salt concentration and high temperature) is applied in the example to reduce background and retain highly specific signals. Two types of probes are selected for the example: the first type of probes are oligonucleotides identical or annealed to SEQ ID NO:1; the second type probes are oligonucleotides partially identical or partially annealed to SEQ ID NO:1. Dot blot method is applied in the example for immobilization of the samples on membrane. The strongest specific signal produced by hybridization between first type probes and samples is obtained after relatively strict membrane washing steps.

Selection of Probes

The principles below should be followed for the selection of oligonucleotide fragments from SEQ ID NO:1 as hybrid probes:

1. The optimal length of probes should be between eighteen and fifty nucleotides.

2. GC amount should be between 30% and 70%, since nonspecific hybridization increases when GC amount is more than 70%.

3. There should be no complementary regions within the probes themselves.

4. Probes meeting the requirements above could be initially selected for further computer-aided sequence analysis, which includes homology comparison between the initially selected probes and its source sequence region (SEQ ID NO: 1), other known genomic sequences and their complements. Generally, the initial selected probes should not be used when they share fifteen identical continuous base pairs, or 85% homology with non-target region.

5. Whether the initially selected probes should be chosen for final application depends upon further experimental confirmation.

The following two probes could be selected and synthesized after the analysis above:

Probe One belongs to the first type, which is completely identical or annealed to the gene fragments of SEQ ID NO: 1 (41 nucleotides):

5'-CAAAAAGAAAGTGATCATATCCTTCCA-GATTCAAAGATGAC-3' (SEQ ID NO: 8)

Probe Two belongs to the second type which is a substituted or mutant sequence of a fragment of SEQ ID NO: 1 (41 nucleotides):

5'-CAAAATCGAAGTGATCATATATCGCCA-GATTCAATCGTGAC-3' (SEQ ID NO: 9)

Any other frequently used reagents unlisted but involved in the following experimental steps and their preparation methods can be found, for example, in: DNA PROBES G. H. Keller; M. M. Manak; Stockton Press, 1989 (USA) or a more commonly used molecular cloning experimental handbook *Molecular Cloning* (J. Sambrook et al. Acadimic press, 1998, 2nd edition)

Sample Preparation

1. DNA Extraction from fresh or frozen tissues

Steps: 1) Place fresh or newly thawed tissue onto a dish on ice containing phosphate-buffered saline (PBS). Cut the tissue into small pieces with scissors or an operating knife. Tissues should be kept damp through the operation. 2) Mince the tissue by centrifugation at 2,000 g for 10 minutes. 3) Re-suspend the pellet (about 10 ml/g) with cold homogenating buffer (0.25 mol/l saccharose; 25 mmol/l Tris-HCl, pH7.5; 25 m mol/LnaCl; 25 mmol/L MgCl2) at 4° C., and homogenate tissue suspension at full speed with an electronic homogenizer until it's completely smashed. 5) Centrifuge at 1,000 g for 10 minutes. 6) Re-suspend the cell pellet (1–5 ml per 0.1 g initial tissue sample), and centrifuge at 1,000 g for 10 minutes. 7) Re-suspend the pellet with lysis buffer (1–5 ml per 0.1 g initial tissue sample), and continue on to the phenol extraction method.

2. Phenol Extraction of DNA

Steps: 1) Wash cells with 1–10 ml cold PBS buffer and centrifuge at 1000 g for 10 minutes. 2) Re-suspend the precipitated cells with at least 100 μl cold cell lysis buffer (1×108 cells/ml). 3) Add SDS to a final concentration of 1%. Addition of SDS into the cell precipitation before cell re-suspension win cause the formation of large balls by cells which is difficult to be smashed and total production will be reduced. This is especially important when extracting more than $10^7$ cells. 5) Incubate at 50° C. for an hour or shake gently overnight at 37° C. 6) Add an equal volume of phenol: chloroform: isoamyl alcohol (25:24:1) to the DNA solution to be purified in a microcentrifuge tube, and centrifuge for 10 minutes. If the two phases are not clearly separated, the solution should be recentrifuged. 7) remove the water phase to a new tube. 8) add an equal volume of chloroform: isoamyl alcohol (24:1) and centrifuge for 10 minutes. 9) remove the water phase containing DNA to a new tube and then purify DNA by ethanol precipitation.

3. DNA Purification By Ethanol Precipitation

Steps: 1) Add 1/10 vol of 2 mol/L sodium acetate and 2 vol of cold 100% ethanol into the DNA solution, mix and place at −20° C. for an hour or overnight. 2) Centrifuge for 10 minutes. 3) Carefully remove the ethanol. 4) Add 500 μl of cold 70% ethanol to wash the pellet and centrifuge for 5 minutes. 6) Carefully remove the ethanol and invert the tube on absorbent paper to remove remnant ethanol. Air dry for 10–15 minutes to evaporate the ethanol on the pellet surface. Do not dry the pellet completely since completely dry pellet is difficult to be dissolved again. 7) Re-suspend the DNA pellet with a small volume of TE or water. Spin at low speed or blow with a pipette, and add TE gradually and mix until DNA is completely dissolved. About 1 μl of DNA solution is obtained per 1~5×$10^6$ cells.

The following steps 8–13 are applied only when contamination must be removed, otherwise go directly to step 14. 8) Add Rnase A into DNA solution to a final concentration of 100 μg/ml and incubate at 37° C. for 30 minutes. 9) Add SDS and protease K to the final concentration of 0.5% and 100 μg/ml individually, and incubate at 37° C. for 30 minutes. 10) Add an equal volume of phenol: chloroform: isoamyl alcohol (25:24:1), and centrifuge for 10 minutes. 11) Carefully remove the water phase and extract it with an equal volume of chloroform: isoamyl alcohol (24:1) and centrifuge for 10 minutes. 12) Carefully remove out the water phase, and add 1/10 vol of 2 mol/L sodium acetate and 2.5 vol of cold 100% ethanol, then mix and place at −20° C. for an hour. 13) Wash the pellet with 70% ethanol and 100% ethanol, air dry and re-suspend DNA as same as the steps 3–6. 14) Determine the purity and production of DNA by A260 and A280 assay. 15) Separate DNA sample into several portions and store at −20° C.

Preparation of Sample Membrane

1) Take 4×2 pieces of nitrocellulose membrane (NC membrane) of desired size, and lightly mark out the sample dot sites and sample number with a pencil. Every probe needs two pieces of NC membrane, so then membranes could be washed under high stringency condition and moderate stringency condition individually in the following experimental steps.

2) Pipette 15 μl of samples and control individually, dot them on the membrane, and dry at room tempreture.

3) Place the membranes on filter paper soaked in 0.1 mol/LnaOH, 1.5 mol/L NaCl, leave for 5 minutes (twice), and allow to dry. Transfer the membranes on filter paper soaked in 0.5 mol/L Tris-HCl (pH7.0), 3 mol/L NaCl, leave for 5 minutes (twice), and allow to dry.

4) place the membranes between clean filter paper, packet with aluminum foil, and vacuum dry at 60–80° C. for 2 hours.

Labeling of Probes

1) Add 3 μl probe (0.1OD/10 μl), 2 μl kinase buffer, 8–10 uCi γ-32P-dATP+2U Kinase, and add water to the final volume of 20 μl.

2) Incubate at 37° C. for 2 hours.

3) Add 1/5 vol bromophenol blue indicator (BPB).

4) Load that sample on Sephadex G-50 column.

5) Collect the first peak before the elution of 32P-Probe (monitor the eluting process by Monitor).

6) Five drops each tube and collect for 10–15 tubes.

7) Measure the isotope amount with liquid scintillator.

8) Merged collection of the first peak is the prepared 32P-Probe (the second peak is free γ-32P-dATP).

Prehybridization

Place the sample membranes in a plastic bag, add 3–10 mg prehybrid buffer (10×Denhardt, s; 6×SSC, 0.1 mg/ml CT DNA (calf thymus gland DNA)), seal the bag, and shake on a 68° C. water bath for two hours hybridization.

Cut off a corner of the plastic bag, add in prepared probes, seal the bag, and shake on a 42° C. water bath overnight.

Membrane Washing

Membrane washing applying a high-stringency condition:

1) Take out the hybridized sample membranes

2) Wash the membranes with 2×SSC, 0.1% SDS at 40° C. for 15 minutes (twice).

3) Wash the membranes with 0.1×SSC, 0.1% SDS at 40° C. for 15 minutes (twice).

4) Wash the membranes with 0.1×SSC, 0.1% SDS at 55° C. for 30 minutes (twice), and dry at room temperature.

Membrane washing applying a low-stringency condition:

1) Take out the hybridized sample membranes.

2) Wash the membranes with 2×SSC, 0.1% SDS at 37° C. for 15 minutes (twice).

3) Wash the membranes with 0.1×SSC, 0.1% SDS at 37° C. for 15 minutes (twice).

4) Wash the membranes with 0.1×SSC, 0.1% SDS at 40° C. for 15 minutes (twice), and dry at room temperature.

X ray Autoradiography

X ray autoradiograph at −70° C. (autoradiograph time varies according to radioactivity of the hybrid spots).

Experimental Results

In hybridization experiments carried out under low-stringency membrane washing condition, the radioactivity of all the above four probes hybridization spots show no obvious difference; while in hybridization experiments carried out under high-stringency membrane washing condition, radioactivity of the hybridization spot by Probe One is obviously stronger than the other three. So Probe One could be applied in qualitative and quantitative analysis of the existence and differential expression of the polynucleotide of the invention in different tissues.

Industrial Applicability

The polypeptide of the invention and antagonists, agonists and inhibitors thereof can be directly used for the treatment of diseases, e.g., various malignant tumors or cancers, dermatitis, inflammation, adrenoprival disease and HIV infection and immune system diseases.

Calcium binding protein family is a large protein super family with many members such as calmodulin, calcyphosine and so on. All members of this super family have a calcium binding motif named "EF-hand." Members of this family play an important role in the regulation of some major physiological process, such as muscle contraction, glycogen metabolism and neurotransmitter release. Its abnormal expression will lead to diseases related to the abnormal release of neurotransmitter, such as nervous system development disorder, nervous system regressive diseases, neuromuscular disorder, nerve-skin syndrome and so on.

The new human calcium binding protein 42, its fragment and derivatives could all be used for diagnosis and treatment of diseases related to the abnormal release of neurotransmitter. These diseases include, but are not limited to: nervous system development disorder such as bifid spine, anencephalus, Encephalocele (cystic cranioschisis), Schizencephaly (cranioschisis), neural tube cyst, Schizencephalic porencephaly, grus formation disorder, Aqueduct deformity, Cerebellar hypoplasia, Down syndrome, Deformity of spinal cord, congenital hydrocephalus, congenital dysgenesis of nuclei of cranial nerves syndrome.

Nervous system degenerative diseases include senile dementia, Parkinson's disease, multiple sclerosis, chorea, melancholia, amnesia, Huntington's disease, epilepsy, megrim, amentia and so on.

Neuromuscular disorders include myasthenia gravis, carina myatrophy, Muscle pseudohypertrophy, Duchenne muscular dystrophy, myotonic dystrophy, muscular tension, dyskinesia, myodystonia and so on.

Nerve-skin syndromes include neurofibromatosis, tuberous sclerosis, Encephalotrigeminal angiomatosis, ataxia telangiectasia and so on.

Diseases of spinal cord include acute myelitis, compressive myelopathy and so on.

Diseases of peripheral nerve include Tic douloureux, facial paralysis, medulla oblongata paralysis, sciatica, greenbaly's syndrome and so on.

Intracranial spaceoccupying lesion include gliocytoma, meningioma, fibroneuroma, pituitary adenoma, Intracranial granuloma and so on.

The new human calcium binding protein 42 of the invention is a kind of calcyphosine. Possibly it is also expressed in olfactory receptor nerves and regulates the olfactory signal transduction. Thus this protein could be used for diagnosis and treatment of diseases related to olfactory nerve tissues such as loss of olfactory sense.

The new human calcium binding protein 42 of the invention could also be used for diagnosis and treatment of congenital diseases related to nervous system. These include, but are not limited to, the following diseases: congenital heart disease, congenital olfaction nerve atrophy, congenital hydrocephalus and so on.

The invention also provides methods for screening compounds so as to identify an agent which enhances human calcium binding protein 42 activity (agonists) or decrease human calcium binding protein 42 activity (antagonists). The agonists enhance the biological functions of human calcium binding protein 42 such as inactivation of cell proliferation, while the antagonists prevent and cure the disorders associated with the excess cell proliferation, such as various cancers. For example, in the presence of an agent, the mammal cells or the membrane preparation expressing human calcium binding protein 42 can be incubated with the labeled human calcium binding protein 42 to determine the ability of the agent to enhance or repress the interaction.

Antagonists of human calcium binding protein 42 include antibodies, compounds, receptor deletants and analogues. The antagonists of human calcium binding protein 42 can bind to human calcium binding protein 42 and eliminate or reduce its function, or inhibit the production of human calcium binding protein 42, or bind to the active site of said polypeptide so that the polypeptide can not function biologically.

When screening for compounds as an antagonist, human calcium binding protein 42 may be added into a biological assay. It can be determined whether the compound is an antagonist or not by determining its effect on the interaction between human calcium binding protein 42 and its receptor. Using the same method as that for screening compounds, receptor deletants and analogues acting as antagonists can be selected. Polypeptide molecules capable of binding to human calcium binding protein 42 can be obtained by screening a polypeptide library comprising various combinations of amino acids bound onto a solid matrix. Usually, human calcium binding protein 42 is labeled in the screening.

The invention further provides a method for producing antibodies using the polypeptide, and its fragment, derivative, analogue or cells as an antigen. These antibodies may be polyclonal or monoclonal antibodies. The invention also provides antibodies against epitopes of human calcium binding protein 42. These antibodies include, but are not limited to, polyclonal antibody, monoclonal antibody, chimeric antibody, single-chain antibody, Fab fragment and the fragments produced by a Fab expression library.

Polyclonal antibodies can be prepared by immunizing animals, such as rabbit, mouse, and rat, with human calcium binding protein 42. Various adjuvants, including but are not limited to Freund's adjuvant, can be used to enhance the immunization. The techniques for producing human calcium binding protein 42 monoclonal antibodies include, but are not limited to, the hybridoma technique (Kohler and Milstein. Nature, 1975, 256: 495–497), the trioma technique, the human B-cell hybridoma technique, the EBV-hybridoma technique and so on. A chimeric antibody comprising a constant region of human origin and a variable region of non-human origin can be produced using methods well-known in the art (Morrison et al, PNAS, 1985, 81:6851). Furthermore, techniques for producing a single-chain antibody (U.S. Pat. No. 4,946,778) are also useful for preparing single-chain antibodies against human calcium binding protein 42.

The antibody against human calcium binding protein 42 can be used in immunohistochemical method to detect the presence of human calcium binding protein 42 in a biopsy specimen.

The monoclonal antibody specific to human calcium binding protein 42 can be labeled by radioactive isotopes, and injected into human body to trace the location and distribution of human calcium binding protein 42. This radioactively labeled antibody can be used in the non-wounding diagnostic method for the determination of tumor location and metastasis.

Antibodies can also be designed as an immunotoxin targeting a particular site in the body. For example, a monoclonal antibody having high affinity to human calcium binding protein 42 can be covalently bound to bacterial or plant toxins, such as diphtheria toxin, ricin, ormosine. One common method is to challenge the amino group on the antibody with sulfydryl cross-linking agents, such as SPDP, and bind the toxin onto the antibody by interchanging the disulfide bonds. This hybrid antibody can be used to kill human calcium binding protein 42-positive cells.

The antibody of the invention is useful for the therapy or the prophylaxis of disorders related to the human calcium binding protein 42. The appropriate amount of antibody can be administrated to stimulate or block the production or activity of human calcium binding protein 42.

The invention further provides diagnostic assays for quantitative and in situ measurement of human calcium binding protein 42 level. These assays are well known in the art and include FISH assay and radioimmunoassay. The level of human calcium binding protein 42 detected in the assay can be used to illustrate the importance of human calcium binding protein 42 in diseases and to determine the diseases associated with human calcium binding protein 42.

The polypeptide of the invention is useful in the analysis of polypeptide profile. For example, the polypeptide can be specifically digested by physical, chemical, or enzymatic means, and then analyzed by one, two or three dimensional gel electrophoresis, preferably by spectrometry.

New human calcium binding protein 42 polynucleotides also have many therapeutic applications. Gene therapy technology can be used in the therapy of abnormal cell proliferation, development or metabolism, which are caused by the loss of human calcium binding protein 42 expression or the abnormal or non-active expression of human calcium binding protein 42. Recombinant gene therapy vectors, such as virus vectors, can be designed to express mutated human calcium binding protein 42 so as to inhibit the activity of endogenous human calcium binding protein 42. For example, one form of mutated human calcium binding protein 42 is a truncated human calcium binding protein 42 whose signal transduction domain is deleted. Therefore, this mutated human calcium binding protein 42 can bind the downstream substrate without the activity of signal transduction. Thus, the recombinant gene therapy vectors can be used to cure diseases caused by abnormal expression or activity of human calcium binding protein 42. The expression vectors derived from a virus, such as retrovirus, adenovirus, adeno-associated virus, herpes simplex virus, parvovirus, and so on, can be used to introduce the human calcium binding protein 42 gene into the cells. The methods for constructing a recombinant virus vector harboring human calcium binding protein 42 gene are described in the literature (Sambrook, et al. supra). In addition, the recombinant human calcium binding protein 42 gene can be packed into liposome and then transferred into the cells.

The methods for introducing the polynucleotides into tissues or cells include directly injecting the polynucleotides into tissue in the body; or introducing the polynucleotides into cells in vitro with vectors, such as virus, phage, or plasmid, etc, and then transplanting the cells into the body.

Also included in the invention are ribozyme and the oligonucleotides, including antisense RNA and DNA, which inhibit the translation of the human calcium binding protein 42 mRNA. Ribozyme is an enzyme-like RNA molecule capable of specifically cutting certain RNA. The mechanism is nucleic acid endo-cleavage following specific hybridization of ribozyme molecule and the complementary target RNA. Antisense RNA and DNA as well as ribozyme can be prepared by using any conventional techniques for RNA and DNA synthesis, e.g., the widely used solid phase phosphite chemical method for oligonucleotide synthesis. Antisense RNA molecule can be obtained by the in vivo or in vitro transcription of the DNA sequence encoding said RNA, wherein said DNA sequence is integrated into the vector and downstream of the RNA polymerase promoter. In order to increase its stability, a nucleic acid molecule can be modified in many manners, e.g., increasing the length of two the flanking sequences, replacing the phosphodiester bond with the phosphothioester bond in the oligonucleotide.

The polynucleotide encoding human calcium binding protein 42 can be used in the diagnosis of human calcium binding protein 42 related diseases. The polynucleotide encoding human calcium binding protein 42 can be used to detect whether human calcium binding protein 42 is expressed or not, and whether the expression of human calcium binding protein 42 is normal or abnormal in the case of diseases. For example, human calcium binding protein 42 DNA sequences can be used in the hybridization with biopsy samples to determine the expression of human calcium binding protein 42. The hybridization methods include Southern blotting, Northern blotting and in situ blotting, etc., which are well-known and established techniques. The corresponding kits are commercially available. A part of or all of the polynucleotides of the invention can be used as probe and fixed on a microarray or DNA chip for analysis of differential expression of genes in tissues and for the diagnosis of genes. The human calcium binding protein 42 specific primers can be used in RNA-polymerase chain reaction and in vitro amplification to detect transcripts of human calcium binding protein 42.

Further, detection of mutations in human calcium binding protein 42 gene is useful for the diagnosis of human calcium binding protein 42 -related diseases. Mutations of human calcium binding protein 42 include site mutation, translocation, deletion, rearrangement and any other mutations compared with the wild-type human calcium binding protein 42 DNA sequence. The conventional methods, such as Southern blotting, DNA sequencing, PCR and in situ blotting, can be used to detect a mutation. Moreover, mutations sometimes affects the expression of protein. Therefore, Northern blotting and Western blotting can be used to indirectly determine whether the gene is mutated or not.

Sequences of the present invention are also valuable for chromosome identification. The sequence is specifically targeted to and can hybridize with a particular location on an individual human chromosome. There is a current need for identifying particular sites of gene on the chromosome. Few chromosome marking reagents based on actual sequence data (repeat polymorphism) are presently available for marking chromosomal location. The mapping of DNA to chromosomes according to the present invention is an important first step in correlating those sequences with genes associated with disease.

Briefly, sequences can be mapped to chromosomes by preparing PCR primers (preferably 15–35 bp) from the cDNA. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the oligonucleotide primers of the invention, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis.

Next, it is necessary to determine the differences in the cDNA or genomic sequence between affected and unaffected individuals. If a mutation is observed in some or all of the affected individuals but not in any normal individuals, then the mutation is likely to be the cause of the disease. Comparison of affected and unaffected individuals generally involves first looking for structural alterations in the chromosomes, such as deletions or translocations, that are visible from chromosome level, or detectable using PCR based on that DNA sequence. With current resolution of physical mapping and genetic mapping techniques, a cDNA precisely localized to a chromosomal region associated with the disease could be one of 50 to 500 potential causative genes. (This assumes 1 megabase mapping resolution and one gene per 20 kb).

According to the invention, the polypeptides, polynucleotides and its mimetics, agonists, antagonists and inhibitors may be employed in combination with a suitable pharmaceutical carrier. Such a carrier includes but is not limited to water, glucose, ethanol, salt, buffer, glycerol, and combinations thereof. Such compositions comprise a safe and effective amount of the polypeptide or antagonist, as well as a pharmaceutically acceptable carrier or excipient with no influence on the effect of the drug. These compositions can be used as drugs in disease treatment.

The invention also provides a pharmaceutical pack or kit comprising one or more containers filled with one or more of the ingredients of the pharmaceutical compositions of the invention. With such container(s) there may be a notice from a governmental agency, that regulates the manufacture, use or sale of pharmaceuticals or biological products, the notice reflects government's approval for the manufacture, use or sale for human administration. In addition, the polypeptides of the invention may be employed in conjunction with other therapeutic compounds.

The pharmaceutical compositions may be administered in a convenient manner, such as through topical, intravenous, intraperitoneal, intramuscular, subcutaneous, intranasal or intradermal routes. human calcium binding protein 42 is administered in an amount, which is effective for treating and/or prophylaxis of the specific indication. The amount of human calcium binding protein 42 administered on patient will depend upon various factors, such as delivery methods, the subject health, the judgment of the skilled clinician.

We claim:

1. An isolated polypeptide having a calcium binding protein 42 activity and comprising an amino acid sequence that is at least 95% identical to SEQ ID NO: 2.

2. The polypeptide of claim 1 wherein said polypeptide comprises the amino acid sequence of SEQ ID NO: 2.

3. A method for detecting a disease related to the polypeptide of claim 1, or for determining a susceptibility of a mammal thereto, said method comprising detecting the activity of said polypeptide.

4. A pharmaceutical composition comprising a polypeptide according of claim 1, and a pharmaceutically acceptable carrier.

5. A method for screening a candidate compound for calcium binding protein 42 mimetic, agonist, antagonist or inhibitory activity comprising a) labeling a human calcium binding polypeptide 42 according to claim 1, b) contacting said labeled polypeptide with a candidate compound and c) identifying mimetic, agonist, antagonist or inhibitory activity.

6. A method for peptide profiling comprising a) labeling a human calcium binding polypeptide 42 according to claim 1, b) digesting said labeled polypeptide to cleave it into fragments and c) analyzing the fragments to determine their profile.

* * * * *

SEQUENCE LISTING

```
<160> NUMBER OF SEQ ID NOS: 9

<210> SEQ ID NO 1
<211> LENGTH: 3829
<212> TYPE: DNA
<213> ORGANISM: Homo sapiens
<220> FEATURE:
<221> NAME/KEY: CDS
<222> LOCATION: (1022)..(2170)
<223> OTHER INFORMATION:

<400> SEQUENCE: 1
gggggagagg aggggaaagc tagacctgca gagtgaagaa agctggtaat agatgtctga      60
caaactaaag aaagacttgt gttaccacaa ttcagacagc ccggaatatc aagattcatc     120
tttttcacta attgtggcat tcacagatgc aaagtattgt tcctgggtgt gtctgtgaga     180
gtattgccaa aggagagcag tgaactggga aaagcagacc cacctcaatg tgggtgggca     240
acatccaatc ggctgccagc tagaataaac caggcaggag aagatggaag agccgacttg     300
ctgaatcttc cagccttcat ctttctcgtg tgctggatgc ttcctgccct caaacatcag     360
actccaggtt cttcgtcttt tggactctcg gatttacatc agtggtttac caggtgctct     420
caggccttca gccacacact gaaggctgaa ttgtcggctt cccgactttt gagattttga     480
aacttggact gagctactgc tggcttcctt gcttctcaac ttacagatgg gacttcacct     540
atagatcatc aaaggtggac ttctgagtca tggacaaacc agaattcttg cccaccagtg     600
gtcccacgac ttgatttggg aagccttgtt gactctgatg atgaggatca gaacataata     660
cctgaaaatt tgccagcacc aacagacaaa tgtaaactaa aatatcagca atgtaaaact     720
gaaattaaag agggctataa gcagtatagt cagagaaatg cagaaaatac aaaatcaaat     780
```

-continued

```
gttacacata aacagtctcc aagaaacaag atagatgaaa agtgtgtgca agatgaagaa      840
gccaacacag atgaccttac gactctggat aggaaagcca tcttacagca aggttatgca      900
gacaactctt gcgataaaca acagagggca agaaaatttg atgcagtaag ttgtcagcat      960
ttttacttat ttggaaattg tggctgcaga gaagaagaaa cagattgttg cagagcaagt     1020 g atg ata gac cac tta tct agg gct gtc atc agt gat cca gag caa aat    1069
  Met Ile Asp His Leu Ser Arg Ala Val Ile Ser Asp Pro Glu Gln Asn
  1               5                  10                  15 tta gcc att gag caa aaa gaa agt gat cat atc ctt cca gat tca aag      1117
Leu Ala Ile Glu Gln Lys Glu Ser Asp His Ile Leu Pro Asp Ser Lys
            20                  25                  30 atg aca cct ctt cga ttt aga aaa aga aca cta cat gaa aca aag ata      1165
Met Thr Pro Leu Arg Phe Arg Lys Arg Thr Leu His Glu Thr Lys Ile
        35                  40                  45 aga act cat tct aca tta act gaa aat gtg ctt tct cat aaa tta cag      1213
Arg Thr His Ser Thr Leu Thr Glu Asn Val Leu Ser His Lys Leu Gln
    50                  55                  60 ttt gat ggt agg atc gta tca cgt aat gga cgt gat gct tgc aga gag      1261
Phe Asp Gly Arg Ile Val Ser Arg Asn Gly Arg Asp Ala Cys Arg Glu
65                  70                  75                  80 ctc att ggg ttc ttt ttc act cat gac caa tcc ctt aca att tat gaa      1309
Leu Ile Gly Phe Phe Phe Thr His Asp Gln Ser Leu Thr Ile Tyr Glu
                85                  90                  95 tat cga caa ttt ggg aaa aat aga aca aat gtg ctt cct ttt att caa      1357
Tyr Arg Gln Phe Gly Lys Asn Arg Thr Asn Val Leu Pro Phe Ile Gln
            100                 105                 110 aaa agc att tat agt cat cag tgt gga cga aga aaa gga aaa caa tac      1405
Lys Ser Ile Tyr Ser His Gln Cys Gly Arg Arg Lys Gly Lys Gln Tyr
        115                 120                 125 cga ctt ggt gat ttt tat gtt ggt gca acc ttg aca ttt ttg agt tct      1453
Arg Leu Gly Asp Phe Tyr Val Gly Ala Thr Leu Thr Phe Leu Ser Ser
    130                 135                 140 gat cat ctc agc ctt cca gaa agc atc aaa gaa aac aca tta ctt aaa      1501
Asp His Leu Ser Leu Pro Glu Ser Ile Lys Glu Asn Thr Leu Leu Lys
145                 150                 155                 160 ctc cga atc aca aat att gat caa ata gct ttg gat tct ctc aaa act      1549
Leu Arg Ile Thr Asn Ile Asp Gln Ile Ala Leu Asp Ser Leu Lys Thr
                165                 170                 175 gct tct atg gaa cag gag gat gat ata atc att caa gaa acc aat gat      1597
Ala Ser Met Glu Gln Glu Asp Asp Ile Ile Ile Gln Glu Thr Asn Asp
            180                 185                 190 agg ctg gtc ttc aaa gca att caa gat gtg cta aaa gaa aaa cta cat      1645
Arg Leu Val Phe Lys Ala Ile Gln Asp Val Leu Lys Glu Lys Leu His
        195                 200                 205 aaa aga ggt gtt cgt att ttg act gga ttg gga aaa tat ttt caa cag      1693
Lys Arg Gly Val Arg Ile Leu Thr Gly Leu Gly Lys Tyr Phe Gln Gln
    210                 215                 220 ttg gac aag gaa gga aat gga ctt tta gat aag gca gat ttt aag caa      1741
Leu Asp Lys Glu Gly Asn Gly Leu Leu Asp Lys Ala Asp Phe Lys Gln
225                 230                 235                 240 gct cta aaa gtg ttt cac tta gaa gtg tct gaa aag gat ttt gag tct      1789
Ala Leu Lys Val Phe His Leu Glu Val Ser Glu Lys Asp Phe Glu Ser
                245                 250                 255 gca tgg cta att ctg aat gac aat ggc aat ggc aag gtt gat tat gga      1837
Ala Trp Leu Ile Leu Asn Asp Asn Gly Asn Gly Lys Val Asp Tyr Gly
            260                 265                 270 gaa ttc aaa cgt ggt att att ggt gaa atg aat gaa tac agg aaa tca      1885
Glu Phe Lys Arg Gly Ile Ile Gly Glu Met Asn Glu Tyr Arg Lys Ser
        275                 280                 285
```

```
tat gtt cga aag gcc ttt atg aaa ctg gat ttc aac aaa agt ggc agt      1933
Tyr Val Arg Lys Ala Phe Met Lys Leu Asp Phe Asn Lys Ser Gly Ser
    290                 295                 300 gtg cct att ata aac ata aga aaa tgt tac tgt gca aag aag cat tct      1981
Val Pro Ile Ile Asn Ile Arg Lys Cys Tyr Cys Ala Lys Lys His Ser
305                 310                 315                 320 caa gta att tca ggc cat tca aca gag gaa gaa atc aaa tca tcc ttt      2029
Gln Val Ile Ser Gly His Ser Thr Glu Glu Glu Ile Lys Ser Ser Phe
                325                 330                 335 cta gaa aca tta aaa gtt gcc tgc agc aag tct gat gaa gtg tca tat      2077
Leu Glu Thr Leu Lys Val Ala Cys Ser Lys Ser Asp Glu Val Ser Tyr
            340                 345                 350 ggt gaa ttt gaa gat tac tat gaa ggt tta agt ata gga ata gta gat      2125
Gly Glu Phe Glu Asp Tyr Tyr Glu Gly Leu Ser Ile Gly Ile Val Asp
        355                 360                 365 gat gaa gac ttt gtt aac atc tta cgt act cca tgg ggg att tag          2170
Asp Glu Asp Phe Val Asn Ile Leu Arg Thr Pro Trp Gly Ile
    370                 375                 380 tctttaataa tacatatgtc atcaacacta agcattttat tggagagatg atatcaatgt    2230
aaaggatgat caaacactgg aatatatttt cctaggactt cctttattct ggtttcttgt    2290
ttgtttgttt tgttttgttt tgttttctca aaaatgttga atttggaaag agaactatcc    2350
agaaagatag atgtagggt gtgttagtgt ttgtgcatgt gtatgcctgt tcacatgtcc     2410
ttacatttgt aaagatatct ttttggttta ttacttatct tgcgtatatt ttagaggtca    2470 tttttttatta acttcagtag gaaagttaca tctgcatcaa acaatatggc aacatctatt   2530
tattaaccaa gtttcctgtc ctttcacatt gttttttgct acctcttcct cagaatatat    2590
ttgccaccat ggcaatttga taaattagaa ttgggcccaa agccagtgag ataattcaat    2650
gtgtttttaa cacatgaaat attaaaggat atgcaagaga aattttttcaa gcagtgtgat   2710 tatagatgtt ttctgtatat agaatatttc aaatgatgga ggtttacccc atgatgctca    2770
tttaaatact gacttgtctt ttaaatctgt cttctaaatt atgtactgtt gttggttaaa    2830
tagagcacaa tgtagttatt ctaatgccca gttgtatttg ttcttttatt ctgcttttta    2890
actgtaatcc tttttaccag catacgattg ttattgagca atatgaaagg gaaatgttct    2950
ttattaaaat caatacatta tcttattaaa caaagatcct aaaagtatat tgttgcatat    3010
atgaatccaa ggaatagttc agtaattatt gcctaaaatg tgaaagcata ttttgtatcc    3070
taaaatgaat gtatgatatt ctaaacatct gttttagtat aacaaacaat tgaaacattt    3130
ccttctaaat atatgttatt taatagttac atgtattata atcattcttt ctaaattctt    3190
tgctagtcat ttcttcctgg gaatacagag aaaagagaca actttatgag ttgttttcaa    3250
cttcataatt ttaaattttc tatgttaata taacataaat tagaaaaaat aagtgattca    3310
aaatgaaaat atttactttg tagaatatga ctttagacat atcactgtat ccatctatac    3370
ttggcagcaa catgagaagt gtgatacatg tgaacccaac aaattcaaag ttgcactttt    3430
caagatgtga gaaggtacta aaacttaata ctaaaacatg agagggaaaa tatgtgtaaa    3490
cctctagtgc tattttcact ggctaaattc tttatttctt gatttttta aaaattaggt    3550 tattaaaatt aaaacaatat gctagaagac attttggcag aaataagtct ataacactat    3610
ttttgtcaca tatctttttc ttggaaaaat ttatccaact atagacatct taaaccctac    3670
aaattgttct tgttaaaaat gactaatact ggggtgctc aatatgcata tagtgttttt     3730
cattgataat tttatttag ttcttaagaa acctgttctc aatgttggca tgtcacattt     3790
```

```
ttctgttact ataatcagaa aatgtatagt ctgttatac                              3829
```

<210> SEQ ID NO 2
<211> LENGTH: 382
<212> TYPE: PRT
<213> ORGANISM: Homo sapiens

<400> SEQUENCE: 2

```
Met Ile Asp His Leu Ser Arg Ala Val Ile Ser Asp Pro Glu Gln Asn
1               5                   10                  15

Leu Ala Ile Glu Gln Lys Glu Ser Asp His Ile Leu Pro Asp Ser Lys
            20                  25                  30

Met Thr Pro Leu Arg Phe Arg Lys Arg Thr Leu His Glu Thr Lys Ile
        35                  40                  45

Arg Thr His Ser Thr Leu Thr Glu Asn Val Leu Ser His Lys Leu Gln
    50                  55                  60

Phe Asp Gly Arg Ile Val Ser Arg Asn Gly Arg Asp Ala Cys Arg Glu
65                  70                  75                  80

Leu Ile Gly Phe Phe Thr His Asp Gln Ser Leu Thr Ile Tyr Glu
                85                  90                  95

Tyr Arg Gln Phe Gly Lys Asn Arg Thr Asn Val Leu Pro Phe Ile Gln
                100                 105                 110

Lys Ser Ile Tyr Ser His Gln Cys Gly Arg Arg Lys Gly Lys Gln Tyr
            115                 120                 125

Arg Leu Gly Asp Phe Tyr Val Gly Ala Thr Leu Thr Phe Leu Ser Ser
        130                 135                 140

Asp His Leu Ser Leu Pro Glu Ser Ile Lys Glu Asn Thr Leu Leu Lys
145                 150                 155                 160

Leu Arg Ile Thr Asn Ile Asp Gln Ile Ala Leu Asp Ser Leu Lys Thr
                165                 170                 175

Ala Ser Met Glu Gln Glu Asp Ile Ile Gln Glu Thr Asn Asp
            180                 185                 190

Arg Leu Val Phe Lys Ala Ile Gln Asp Val Leu Lys Glu Lys Leu His
        195                 200                 205

Lys Arg Gly Val Arg Ile Leu Thr Gly Leu Gly Lys Tyr Phe Gln Gln
    210                 215                 220

Leu Asp Lys Glu Gly Asn Gly Leu Leu Asp Lys Ala Asp Phe Lys Gln
225                 230                 235                 240

Ala Leu Lys Val Phe His Leu Glu Val Ser Glu Lys Asp Phe Glu Ser
                245                 250                 255

Ala Trp Leu Ile Leu Asn Asp Asn Gly Asn Gly Lys Val Asp Tyr Gly
            260                 265                 270

Glu Phe Lys Arg Gly Ile Ile Gly Glu Met Asn Glu Tyr Arg Lys Ser
        275                 280                 285

Tyr Val Arg Lys Ala Phe Met Lys Leu Asp Phe Asn Lys Ser Gly Ser
    290                 295                 300

Val Pro Ile Ile Asn Ile Arg Lys Cys Tyr Cys Ala Lys Lys His Ser
305                 310                 315                 320

Gln Val Ile Ser Gly His Ser Thr Glu Glu Ile Lys Ser Ser Phe
                325                 330                 335

Leu Glu Thr Leu Lys Val Ala Cys Ser Lys Ser Asp Glu Val Ser Tyr
            340                 345                 350

Gly Glu Phe Glu Asp Tyr Tyr Glu Gly Leu Ser Ile Gly Ile Val Asp
        355                 360                 365
```

Asp Glu Asp Phe Val Asn Ile Leu Arg Thr Pro Trp Gly Ile
            370              375              380

<210> SEQ ID NO 3
<211> LENGTH: 22
<212> TYPE: DNA
<213> ORGANISM: Artificial
<220> FEATURE:
<223> OTHER INFORMATION: oligonucleotide primer

<400> SEQUENCE: 3 ggggagagg agggaaagc ta                                              22

<210> SEQ ID NO 4
<211> LENGTH: 22
<212> TYPE: DNA
<213> ORGANISM: Artificial
<220> FEATURE:
<223> OTHER INFORMATION: oligonucleotide primer

<400> SEQUENCE: 4
gtataacaga ctatacattt tc                                            22

<210> SEQ ID NO 5
<211> LENGTH: 34
<212> TYPE: DNA
<213> ORGANISM: Artificial
<220> FEATURE:
<223> OTHER INFORMATION: oligonucleotide primer

<400> SEQUENCE: 5
ccccatatga tgcagttaac acatcagctg gacc                               34

<210> SEQ ID NO 6
<211> LENGTH: 34
<212> TYPE: DNA
<213> ORGANISM: Artificial
<220> FEATURE:
<223> OTHER INFORMATION: oligonucleotide primer

<400> SEQUENCE: 6
ccccatatga tgatagacca cttatctagg gctg                               34

<210> SEQ ID NO 7
<211> LENGTH: 15
<212> TYPE: PRT
<213> ORGANISM: Artificial
<220> FEATURE:
<223> OTHER INFORMATION: Partial sequence of SEQ ID NO: 2

<400> SEQUENCE: 7

Met Ile Asp His Leu Ser Arg Ala Val Ile Ser Asp Pro Glu Gln
1                5                  10                  15

<210> SEQ ID NO 8
<211> LENGTH: 41
<212> TYPE: DNA
<213> ORGANISM: Artificial
<220> FEATURE:
<223> OTHER INFORMATION: oligonucleotide primer

<400> SEQUENCE: 8
caaaaagaaa gtgatcatat ccttccagat caaagatga c                        41

<210> SEQ ID NO 9
<211> LENGTH: 41

-continued

```
<212> TYPE: DNA
<213> ORGANISM: Artificial
<220> FEATURE:
<223> OTHER INFORMATION: oligonucleotide primer

<400> SEQUENCE: 9
caaaatcgaa gtgatcatat atcgccagat tcaatcgtga c                    41
```